United States Patent [19]

Condon et al.

[11] 4,307,110
[45] Dec. 22, 1981

[54] MERCAPTOACYL DERIVATIVES OF 3-SUBSTITUTED PROLINE DERIVATIVES

[75] Inventors: Michael E. Condon, Lawrenceville; Miguel A. Ondetti, Princeton, both of N.J.

[73] Assignee: E. R. Squibb & Sons, Inc., Princeton, N.J.

[21] Appl. No.: 187,009

[22] Filed: Sep. 12, 1980

[51] Int. Cl.$^3$ .................... C07D 207/12; A61K 31/40
[52] U.S. Cl. ................. 424/274; 260/326.2; 260/326.25; 260/326.43
[58] Field of Search .......... 260/326.2, 326.43, 326.25; 424/274

[56] References Cited

U.S. PATENT DOCUMENTS 4,046,889  9/1977  Ondetti et al. ............ 260/326.2
4,105,776  8/1978  Ondetti et al. ............ 260/326.2
4,154,935  5/1979  Ondetti et al. ............ 260/326.2
4,198,515  4/1980  Ondetti et al. ............ 260/326.25

FOREIGN PATENT DOCUMENTS 2028327  3/1980  United Kingdom ............ 260/326.2

Primary Examiner—John M. Ford
Assistant Examiner—Jane T. Fan
Attorney, Agent, or Firm—Lawrence S. Levinson; Burton Rodney

[57] ABSTRACT

New mercaptoacyl derivatives of 3-substituted proline derivatives are provided which have the general formula

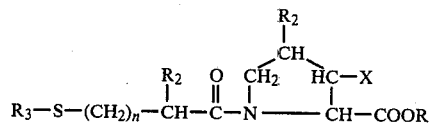

and are useful as hypotensive agents.

10 Claims, No Drawings

MERCAPTOACYL DERIVATIVES OF 3-SUBSTITUTED PROLINE DERIVATIVES

BACKGROUND OF THE INVENTION

U.S. Pat. No. 4,105,776, issued Aug. 8, 1978 to Miguel Angel Ondetti and David W. Cushman, and its parent U.S. Pat. No. 4,046,889, issued Sept. 6, 1977, disclose certain mercaptoacyl derivatives of the naturally occurring amino acids proline and hydroxyproline. These compounds are angiotensin converting enzyme inhibitors which can be used for the reduction of blood pressure.

Ondetti et al. in U.S. Pat. No. 4,154,935 and in application Ser. No. 37,255, filed May 9, 1979, disclose certain mercaptoacyl derivatives of pipecolic acid and proline wherein the hetero ring can have one or more halogen substituents and the mercaptoacyl sidechain can have a halogen, alkyl, or trifluoromethyl substituent. These compounds are also angiotensin converting enzyme inhibitors which can be used for the reduction of blood pressure.

SUMMARY OF THE INVENTION

This invention relates to mercaptoacyl derivatives of 3-substituted prolines of the formula

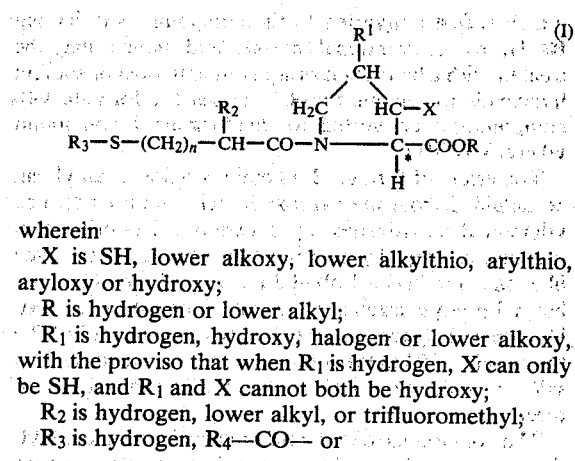

wherein

X is SH, lower alkoxy, lower alkylthio, arylthio, aryloxy or hydroxy;

R is hydrogen or lower alkyl;

$R_1$ is hydrogen, hydroxy, halogen or lower alkoxy, with the proviso that when $R_1$ is hydrogen, X can only be SH, and $R_1$ and X cannot both be hydroxy;

$R_2$ is hydrogen, lower alkyl, or trifluoromethyl;

$R_3$ is hydrogen, $R_4$—CO— or

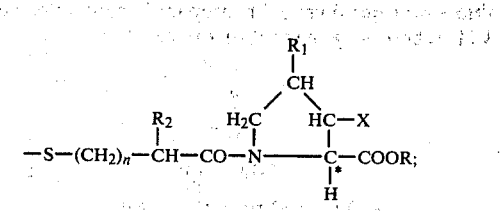

$R_4$ is lower alkyl or phenyl;

n is 0, 1 or 2;

and salts thereof.

DETAILED DESCRIPTION OF THE INVENTION

The invention in its broadest aspects relates to mercaptoacyl derivatives of prolines having formula I above, to compositions containing such compounds and to the method for using such compounds as anti-hypertensive agents.

The term lower alkyl as used in defining the symbols X, R, $R_1$ and $R_2$ are straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl being most preferred.

The terms lower alkoxy and lower alkylthio as used in defining the symbol X or $R_1$ refer to any of the above lower alkyl groups linked to an oxygen or sulfur, respectively.

The terms arylthio and aryloxy as used in defining the symbol X include phenyl, phenyl substituted with one or two halogens, hydroxy, lower alkyl, lower alkoxy, lower alkylthio, cyano or nitro groups, 1-naphthyl, 2-naphthyl, biphenyl linked to a sulfur or oxygen, respectively.

The term halogen includes four common members, i.e., chloro, bromo, fluoro, and iodo, with chloro, bromo, and fluoro being preferred.

The lower alkanoyl groups represented by $R_4$—CO— are those having the acyl radicals of the lower ($C_2$-$C_7$) fatty acids, for example, acetyl, propionyl, butyryl, isobutyryl, and the like. The lower alkanoyl groups having up to four carbons are preferred with acetyl being especially preferred.

The asterisk in formula I indicates an asymmetric center which is present in the proline ring. Of course, an additional asymmetric center can be present in the mercapto sidechain depending upon the substituent $R_2$. The products of formula I accordingly exist in stereoisomeric forms or as racemic mixtures thereof. All of these are within the scope of the invention. The synthesis described below can utilize the racemate or one of the enantiomers as starting materials. When the racemic starting material is used in the synthesis procedure, the stereoisomers obtained in the final product can be separated by conventional chromatographic or fractional crystallization methods. The $R_1$ group also gives rise to cis-trans isomerism.

Preferably the asymmetric center in the proline ring is in the L-configuration and if there is an asymmetric center in the mercaptoacyl sidechain, it is in the D-configuration.

Preferred compounds of formula I are those wherein X is SH, R is hydrogen, $R_1$ is hydrogen, hydroxy, chlorine or methoxy; $R_2$ is hydrogen, methyl, or trifluoromethyl; $R_3$ is hydrogen and n is zero or one. Also preferred as intermediates are the above compounds wherein $R_3$ is acetyl or benzoyl, especially acetyl.

Most preferred are the compounds of formula I wherein X is SH; R is H; $R_1$ is H; $R_2$ is H; $R_3$ is H; and n is 1.

The compounds of formula I having X=SH are prepared from intermediates of formula II which are prepared as described in U.S. Pat. No. 4,198,515.

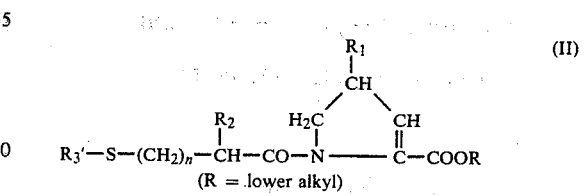

Thus, for example, the ester of the formula II starting materials wherein $R'_3$ is lower alkanoyl or benzoyl may be reacted with a thiol acid,

(R″3 is a lower alkanoyl or benzoyl group which is the same as or different from R′3) such as, thiolacetic acid, to form the ester compound of the invention of the structure

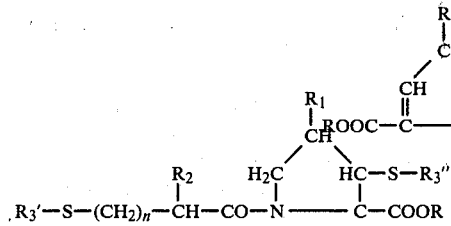

(IV)

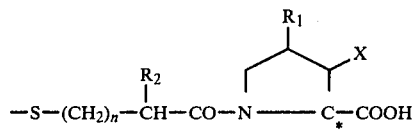

and X is SH, then the starting material

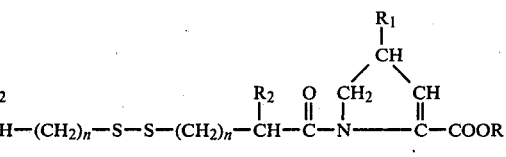

VIa (the preparation of which is described in U.S. Pat. No. 4,198,515) is reacted with a thio acid III to form the compound

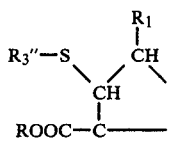

VIb

The ester IV can be converted to the free acid, i.e., R is H, by conventional means. Thus, where R is t-butyl, the ester IV can be treated with trifluoroacetic acid and anisole to form the formula V compound of the invention.

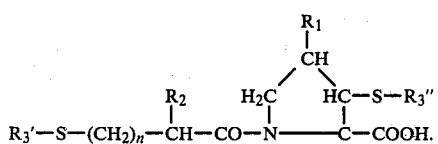

(V)

Treatment of the formula V compound of the invention with a base, such as aqueous ammonia or sodium hydroxide removes the R′3 and R″3 ester groups so that the formula V compound is converted to the formula I compound of the invention where X is SH, that is

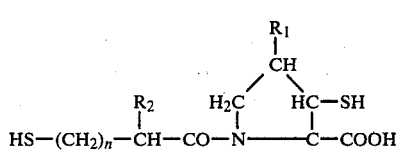

(VI)

The product of formula I wherein R3 is

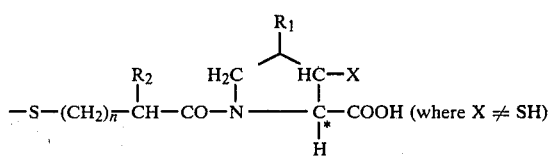

are obtained by directly oxidizing with iodine a product of formula I wherein R3 is hydrogen.

In the case where R3 is which is first converted to the compound VIb having R=H, by conventional means, and which may be treated with a base, such as aqueous ammonia or sodium hydroxide to remove the R″3 so that the formula VIb compound is converted to the formula I compound where X is SH.

The esters of formula I wherein R is lower alkyl can be obtained from the carboxylic acid compounds, i.e., wherein R is hydrogen, by conventional esterification procedures, e.g., by esterification with a diazoalkane like diazomethane, 1-alkyl-3-p-tolyltriazene, like 1-n-butyl-3-p-tolyltriazene, or the like. The esters can also be prepared by treating the acid with an alcohol of the formula R—OH in the presence of a Lewis acid, such as sulfuric acid, boron trifluoride, etc., at room temperature.

The compounds of formula I where X is lower alkylthio or arylthio may be prepared from intermediates VII, where R5 is benzyl or t-butyl

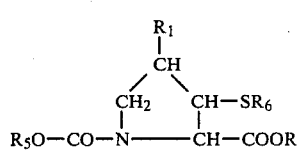

VII and R is lower alkyl. Thus, treatment of compounds VII with a thiol R6SH, where R6 is lower alkyl or aryl, in the presence of sodium methoxide in methanol gives intermediates of formula VIII, which can be deprotected

VIII by means of standard techniques utilized in peptide synthesis to yield amino acids of formula IX

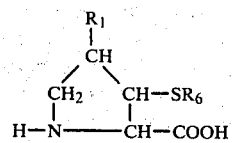

IX

Thus, treatment of intermediates VIII where R₅ is benzyl and R is t-butyl with hydrogen bromide in acetic acid yields acids IX as their hydrobromic acid salts.

Intermediates of formula IX are reacted with an acid chloride.

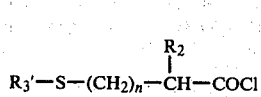

X in the presence of a base, such as sodium carbonate, and ethyl ether to form compounds of structure XI

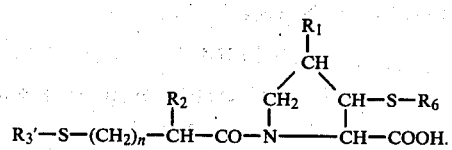

XI

Intermediates of formula VII are prepared from compounds XII (prepared as described in U.S. Pat. No. 4,198,515). Thus,

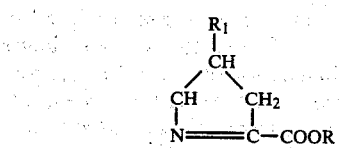

XII compounds of formula VII wherein R is preferably t-butyl are reacted with an acid chloride

where R₅ is benzyl, in an inert solvent, such as dichloromethane, chloroform, benzene, toluene or the like, in the presence of a strong base, such as 1,5-diazabicyclo[5.4.0]undec-5-ene (to dehydrohalogenate the product) at a reduced temperature, for example, in the range of from about −5° to +5° C. to form the intermediate VII.

The compounds of formula I where X is lower alkoxy, aryloxy, or hydroxy are prepared from intermediates XIII. Thus,

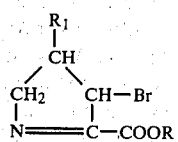

XIII treatment of compounds of formula XIII where R is preferably t-butyl with metal hydroxides, alkoxides, or aryloxides in a solvent, such as N,N-dimethylformamide gives intermediates of formula XIV

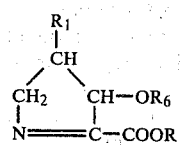

XIV where R₆ is hydrogen, lower alkyl and aryl.

Removal of the ester protecting group from intermediates XIV followed by reduction of the products with sodium borohydride yields amino acids of formula XV

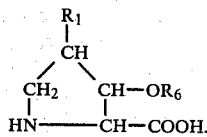

XV

Intermediates of formula XV are treated with an acid chloride

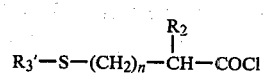

X in the presence of a base, such as sodium carbonate, and ethyl ether to form compounds XVI

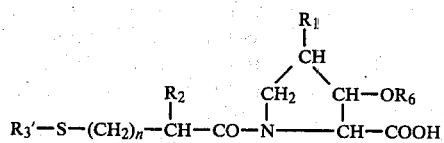

XVI

Compounds of the formula I where X is hydroxyl and R'₃ is hydrogen are prepared by treatment of compounds XVI where R₆ is hydrogen with a base, such as aqueous ammonia or sodium hydroxide to remove the R'₃ ester group.

Intermediates of formula XIII are prepared by brominating intermediates XII according to the procedure of J. Häusler and V. Schmidt, *Liebigs Ann. Chem.*, 1881 (1979).

Reference is also made to the following publications for additional illustrative information with respect to the production of starting materials and intermediates: Ondetti et al., U.S. Pat. Nos. 4,046,889, 4,105,776 and 4,154,935; Neuberger, J. Chem. Soc., 1945, p. 429–432; Patchett et al., J. Amer. Chem. Soc. 79, p. 185–192 (1957); Baer et al., Can. J. Biochem. and Phys., 37, p. 583–587 (1959); Sheehan et al., J. Amer. Chem. Soc. 85, p. 3863–3865 (1963); Magerlein, J. Med. Chem. 10, p. 1161–1163 (1967). The procedures illustrated therein can be utilized as general methods for the synthesis and stereoconversion of compounds utilizable in the invention of this application.

Additional experimental details are found in the examples which are preferred embodiments and also serve as models for the preparation of other members of the group.

The compounds of this invention form basic salts with a variety of inorganic or organic bases. The salt forming ion derived from such bases can be metal ions, e.g., aluminum, alkali metal ions, such as sodium or potassium, alkaline earth metal ions, such as calcium or magnesium, or an amine salt ion, of which a number are known for this purpose, for example, aralkylamines like, dibenzylamine, N,N-dibenzylethylenediamine, lower alkylamines like methylamine, t-butylamine, procaine, lower alkylpiperidines like N-ethylpiperidine, cycloalkylamines like cyclohexylamine or dicyclohexylamine, 1-adamantanamine, benzathine, or salts derived from amino acids like arginine, lysine or the like. The physiologically acceptable salts like the sodium or potassium salts can be used medicinally as described below and are preferred. These and other salts which are not necessarily physiologically acceptable are useful in isolating or purifying a product acceptable for the purposes described below, as illustrated with the dicyclohexylamine salt and the cyclohexylamine salt in the examples. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of this invention inhibit the conversion of the decapeptide angiotensin I to angiotensin II and therefore are useful in reducing or relieving hypertension. The compounds of this invention intervene in the renin→angiotensinogen→angiotensin I→angiotensin II sequence by inhibiting angiotensin converting enzyme and reducing or eliminating the formation of the pressor substance angiotensin II. Thus, by administration of a hypotensively effective amount of a composition containing one or a combination of compounds of formula I or physiologically acceptable salt thereof, hypertension in the species of mammal suffering therefrom is reduced or alleviated.

A single dose, or preferably two to four divided daily doses, provided in a basis of about 0.1 to about 100 mg per kilogram per day, preferably about 1 to about 50 mg per kilogram per day, is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes, such as subcutaneously, intramuscularly, intravenously or intraperitoneally can also be employed.

The compounds of this invention can be utilized to achieve the reduction of blood pressure by formulating in compositions, such as tablets, capsules or elixirs for oral administration or in sterile solutions or suspensions for parenteral administration. About 10 to about 500 mg of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that suitable dosage in the range indicated is obtained.

Illustrative of the adjuvants which may be incorporated in tablets, capsules and the like are the following: a binder, such as gum tragacanth, acacia, corn starch or gelatin; an excipient, such as dicalcium phosphate or microcrystalline cellulose; a disintegrating agent, such as corn starch, potato starch, alginic acid and the like; a lubricant, such as magnesium stearate; a sweetening agent, such as sucrose, lactose or saccharin; a flavoring agent, such as peppermint, oil of wintergreen or cherry.

When the dosage unit form is a capsule, it may contain in addition to materials of the above type a liquid carrier, such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring, such as cherry or orange flavor.

Sterile compositions for injection can be formulated according to conventional pharmaceutical practice by dissolving or suspending the active substance in a vehicle, such as water for injection, a naturally occurring vegetable oil like sesame oil, coconut oil, peanut oil, cottonseed oil, etc.

The following examples are illustrative of the invention and constitute preferred embodiments. They also serve as models for the preparation of other members of the group which can be produced by replacement of the given reactants with suitably substituted analogs. All temperatures are in degrees Celsius.

EXAMPLE 1

(trans)-3-Mercapto-1-(3-mercapto-1-oxopropyl)proline

A.

1-[3-(Acetylthio)-1-oxopropyl]-4,5-dihydro-1H-pyrrole-2-carboxylic acid, t-butyl ester The title A compound (described in U.S. Pat. No. 4,198,515, Example 36) is prepared as follows.

To a stirred solution of 13.52 g (80 mmoles) of freshly distilled 1,2-dehydro proline t-butyl ester in 50 ml of dichloromethane at $-5°$ to $0°$ is added over ten minutes a solution of 13.32 g (80 mmoles) of 3-acetylthiopropanoyl chloride in 50 ml of dichloromethane. During the addition the temperature is maintained at $-5°$ to $0°$, and after the addition is complete the solution is stirred for five minutes.

To this stirred solution at $-5°$ to $0°$ is added dropwise over ten minutes a solution of 12.16 g (80 mmoles) of 1,5-diazabicyclo[5.4.0]-undec-5-ene (DBU) in 50 ml of dichloromethane. After the addition is complete, the cooling bath is removed and the reaction mixture is stirred for one hour.

The solution is washed with cold dilute hydrochloric acid, saturated aqueous sodium bicarbonate, dried, and concentrated in vacuo to a semi-crystalline solid. Two recrystallizations of this material from hexane affords 6.0 g (25%) of crystalline solid, m.p. 59°–62°.

B.

(trans)-3-(Acetylthio)-1-[3-(acetylthio)-1-oxopropyl]-proline, t-butyl ester

A solution of 11.2 g (38 mmol) of 1-[3-(acetylthio)-1-oxopropyl]-4,5-dihydro-1H-pyrrole-2-carboxylic acid, t-butyl ester (prepared as described above) in 60 ml of thiolacetic acid is left standing overnight at room temperature. The mixture is then taken to dryness in vacuo. Toluene is added and removed in vacuo four times. The residue is dissolved in dichloromethane and chromatographed on 400 g silica gel packed in dichloromethane. After removal of some fast moving materials the product is eluted with 1% MeOH in $CH_2Cl_2$. Fractions appearing clean on TLC are combined and, after trituration with isopropyl ether, 4.8 g (34%) of crystalline material is obtained, m.p. 85°–88°.

C.
(trans)-3-(Acetylthio)-1-[3-(acetylthio)-1-oxopropyl]-proline

The crystalline t-butyl ester (4.8 g, 12.8 mmol) from part B is mixed with 14 ml anisole (130 mmol) and cooled in an ice bath. Cold trifluoroacetic acid (65 ml) is then added and the mixture is stirred while cooling in an ice bath for two hours. The trifluoroacetic acid is then removed in vacuo. The residue is dissolved in ether and the product is extracted into saturated NaHCO₃ solution. The aqueous extracts are acidified with HCl and the product is then extracted with ethyl acetate. The ethyl acetate solution is dried and freed of solvent in vacuo leaving a quantitative amount (4.1 g) of white solid. A portion of this (1.5 g) is recrystallized from ethyl acetate to give 1.0 g (67%) of the title C compound, m.p. 145°–148°.

D.
(trans)-3-(Mercapto-1-(3-mercapto-1-oxopropyl)proline (trans)-3-(Acetylthio)-1-[3-(acetylthio)-1-oxopropyl]-proline prepared as described in part C (2.2 g, 6.9 mmol) is cooled in an ice bath under argon and treated with a cold argon saturated mixture of 7 mg of water and 7 ml concentrated NH₄OH. After stirring for thirty minutes, the cold solution is acidified with HCl and the product is extracted into ethyl acetate, dried and freed of solvent in vacuo leaving a quantitative amount of viscous oil.

This oil is dissolved in ethyl acetate and treated with 1 equivalent of distilled dicyclohexylamine. The dicyclohexylamine salt (2.7 g, 94%) crystallizes out. The solution is filtered several times through Celite to remove small amounts of materials. The filtrate is then taken to dryness to give 1.4 g of solid. This is triturated with ethyl acetate to give the title compound in the form of the dicyclohexylamine salt as white crystalline material, m.p. (160°) 170°–176° dec., 0.85 g.

The dicyclohexylamine salt is converted back to the free acid by stirring ten minutes with 10% KHSO₄ solution. The acid is then extracted into ethyl acetate, dried and freed of solvent in vacuo to give the title compound (free acid), 448 mg (28%) as a viscous oil.

EXAMPLE 2

(trans)-3-Mercapto-1-(3-mercapto-2-methyl-1-oxopropyl)proline

A. 1,2-Dehydroproline, t-butyl ester

To a stirred solution of 34.2 g (0.20 mole) of proline t-butyl ester in 600 ml of ether at −5°→0° is added dropwise over ten minutes 21.7 g (23.9 ml=0.20 mole) of freshly prepared t-butyl hypochlorite [*Org. Syn., Coll. Vol. V,* 184 (1973)]. During the addition, the temperature is maintained at −5°→0°. After the addition is complete, the solution is stirred at this temperature for an additional five minutes.

To the vigorously stirred solution is added rapidly (~3-5 min) a solution of 7.8 g (0.20 mole) of potassium in freshly distilled dry (CaH₂) t-butanol. After the addition, the temperature of the reaction mixture is 18°. The reaction vessel is removed from the cooling bath and stirred for thirty minutes. The reaction mixture is filtered through Celite and the filtrate concentrated in vacuo. The residue is taken up in ether and washed with several portions of water. The ether solution is dried and concentrated in vacuo to 36.1 g of yellow liquid. A trace of hydroquinone is added and the crude product distilled, affording 22.4 g (66%), b.p. 60°–62°/0.1 mm.

B.
(±)-1-[3-(Acetylthio)-2-methyl-1-oxopropyl]-4,5-dihydro-1H-pyrrole-2-carboxylic acid, t-butyl ester To a stirred solution of 16.9 g (0.10 mole) of freshly distilled 1,2-dehydroproline t-butyl ester in 60 ml of dichloromethane at −5°→0° is added dropwise over ten minutes, a solution of 18.1 g (0.1 mole) of 3-acetylthio-2-methylpropanoyl chloride in 60 ml of dichloromethane. During the addition, the temperature is maintained at −5°→0°, and after the addition is complete the solution is stirred for five minutes.

To this stirred solution at −5°→0° is added dropwise over ten minutes a solution of 15.2 g (0.10 mole) of 1,5-diazabicyclo[5.4.0]undec-5-ene (DBU) in 60 ml of dichloromethane. After the addition is complete, the cooling bath is removed, and the reaction mixture is stirred for one hour.

The yellow solution is washed with cold dilute hydrochloric acid, saturated aqueous sodium bicarbonate, dried, and concentrated in vacuo to 27.7 g of oil. The oil is taken up in diisopropyl ether and chilled, affording 9.3 g (30%) of crystalline solid, m.p. 77°–80°.

C.
(trans)-3-(Acetylthio)-1-[3-(acetylthio)-2-methyl-1-oxopropyl]proline, t-butyl ester Following the procedure of Example 1B except substituting 1-[3-(acetylthio)-2-methyl-1-oxopropyl]-4,5-dihydro-1H-pyrrole-2-carboxylic acid, t-butyl ester for 1-[3-(acetylthio)-1-oxopropyl]-4,5-dihydro-1H-pyrrole-2-carboxylic acid, t-butyl ester, the title compound is obtained.

D.
(trans)-3-(Acetylthio)-1-[3-(acetylthio)-2-methyl-1-oxopropyl]proline

Following the procedure of Example 1C except substituting the Example 2C crystalline t-butyl ester for the Example 1B ester, the title D compound is obtained.

E.
(trans)-3-Mercapto-1-(3-mercapto-2-methyl-1-oxopropyl)proline

Following the procedure of Example 1C except substituting (trans)-3-(acetylthio)-1-[3-(acetylthio)-2-methyl-1-oxopropyl]proline for (trans)-3-(acetylthio)-1-[3-(acetylthio)-1-oxopropyl]proline, the title compound is obtained.

EXAMPLE 3

(±)-trans-1-[3-(Acetylthio)-1-oxopropyl]-3-methylmercaptoproline

A.
1-Benzyloxycarbonyl-4,5-dihydro-1H-pyrrole-2-carboxylic acid, tert-butyl ester A solution of 1,2-dehydroproline t-butyl ester (prepared as described in Example 2A) (16.9 g, 100 mmol) in 70 ml dichloromethane is cooled to −10° C. under argon. A solution of freshly distilled benzylchloroformate (14.2 ml, 100 mmol, b.p. 62°–64°/0.4 mm) in 70 ml dichloromethane is added dropwise over a period of thirty minutes. After stirring cold another thirty minutes a solution of 1,5-diazabicyclo[5.4.0]undec-5-ene (DBU) (15.22 g, 100 mmol) in 70 ml dichloromethane is added over a period of twenty minutes. The cooling bath is then removed and the mixture is stirred at room temperature for one hour. After washing twice with cold dilute hydrochloride and once with saturated NaHCO$_3$ solution, the solution is dried and freed of solvent in vacuo leaving 18.2 g (60%) of product as a pale yellow oil.

B.
(±)-trans-1-Benzyloxycarbonyl-3-methylmercaptoproline, tert-butyl ester

A solution of the dehydro compound of Part A (18.2 g, 60 mmol) in 180 ml dry methanol is treated with sodium methoxide (3.24 g, 60 mmol) and cooled in an ice bath. Methane thiol is bubbled into the solution slowly for thirty minutes. The mixture is stirred overnight under argon at room temperature. Dilute aqueous acetic acid is added until the solution is slightly acidic. Argon is bubbled through the solution for one hour before it is taken to near dryness in vacuo. Ethyl acetate is added and the solution is washed twice with saturated NaHCO$_3$ solution, dried and freed of solvent in vacuo leaving 17 g foul smelling yellow oil. This is chromatographed using 300 g silica gel (230-400 mesh, EM reagents) using petroleum ether:ether 4:1 (the compound is preabsorbed from ether). The pressure is adjusted so the flow rate is 125 ml/min. Samples are checked on TLC (silica gel; petroleum ether:ether 1:1; I$_2$) and fractions appearing clean are combined to give 11.1 g (53%) of product as a colorless oil.

C. (±)-trans-3-Methylmercaptoproline

The compound described above in Part B (8.4 g, 24 mmol) is treated with 45 ml 4 N HBr in HOAc. After stirring one hour at room temperature the solution is taken to dryness in vacuo. A small amount of water is added and this is washed twice with ether. The aqueous solution is applied to a column containing 300 ml AG50W-X2 resin and water is passed through until the eluate is no longer strongly acidic. The product is then eluted with pH 6.5 (aqueous pyridine acetate)buffer. Fractions positive to ninhydrin are combined and lyophillized to give 3.4 g (88%) of white fluff. A small sample of this is crystallized from methanol to give the title C compound, m.p. (192°) 196°-200° dec.

D.
(±)-trans-1-[3-(Acetylthio)-1-oxopropyl]-3-methylmercaptoproline

3-Methylmercaptoproline from Part C (3.05 g, 18.9 mmol) is dissolved in 19 ml 1 N Na$_2$CO$_3$ and diluted with 10 ml water. The solution is cooled in an ice bath and while stirring rapidly a solution of 3-acetylthiopropionyl chloride in 20 ml ether is added. The pH is maintained at 8 by adding 1 N Na$_2$CO$_3$. At the end of thirty minutes the pH is holding constant and 45 ml of carbonate has been added. The layers are separated and the aqueous is washed once with water. The aqueous is then acidified with 10% KHSO$_4$ solution and the product is extracted into ethyl acetate, dried and freed of solvent in vacuo leaving 5.2 g oil. This is chromatographed on 150 g silica gel (230-400 mesh, EM Reagents) using ethyl acetate for elution. A small sample of the product (3.85 g, 70%) obtained is dissolved in ether and converted to the dicyclohexylamine salt which is recrystallized from ethyl acetate to give the title compound, m.p. 153°-157°.

EXAMPLE 4

1,1'-[Dithiobis(1-oxo-3,1-propanediyl)]bis[trans-3-acetylthioproline]

A.
1,1'-[Dithiobis(1-oxo-3,1-propanediyl)]bis[trans-3-acetylthioproline], t-butyl ester by substituting 1,1'-[dithiobis(1-oxo-3,1-propanediyl)]bis[4,5-dihydro-1H-pyrrole-2-carboxylic acid]tert-butyl ester (described in U.S. Pat. No. 4,198,515, Example 39) for 1-[3-(acetylthio)-1-oxopropyl]-4,5-dihydro-1H-pyrrole-2-carboxylic acid, t-butyl ester in the procedure of Example 1B, 1,1'-[dithiobis(1-oxo-3,1-propanediyl)]bis[trans-3-acetylthioproline]t-butyl ester is obtained.

B.
1,1'-[Dithiobis(1-oxo-3,1-propanediyl)]bis-[trans-3-acetylthioproline]

By substituting 1,1'-[dithiobis(1-oxo-3,1-propanediyl)]bis[trans-3-acetylthioproline], t-butyl ester for (trans)-3-(acetylthio)-1-[3-(acetylthio)-1-oxopropyl]proline t-butyl ester in the procedure of Example 1C, 1,1'-[dithiobis(1-oxo-3,1-propanediyl)]bis[trans-3-acetylthioproline] is obtained.

EXAMPLE 5

1,1'-[Dithiobis(1-oxo-3,1-propanediyl]bis[trans-3-mercaptoproline]

By substituting 1,1'-[dithiobis(1-oxo-3,1-propanediyl)]bis[trans-3-acetylthioproline] (prepared in Example 4) for trans-3-acetylthio-1-[(3-acetyl-thio)-1-oxopropyl]proline in the procedure of Example 1D, 1,1'-[dithiobis(1-oxo-3,1-propanediyl)]-bis[trans-3-mercaptoproline] is obtained.

EXAMPLES 6 TO 13

Following the procedure of Example 1 except by substituting the acid chloride compound listed in Column I of Table I set out below for 3-acetylthiopropanoyl chloride in Part A, and substituting the proline compound listed in Column II for 1,2-dehydro proline t-butyl ester, the compound set out in Column III is obtained; and thereafter by substituting the mercaptan listed in Column IV for thioacetic acid in Part B, the compound set out in Column V is obtained.

TABLE I

| | Column I | | | | Column II | | Column III | | | | | Column IV | Column V | | | | |
|---|---|---|---|---|---|---|---|---|---|---|---|---|---|---|---|---|---|
| | $R_3'-S-(CH_2)_n-CH-COCl$ with $R_2$ | | | |  | | $R_3'-S-(CH_2)_n-CH-CO-N-C-COOR$ with $R_2$, $R_1$ | | | | | $R_3''SH$ | $R_3'-S-(CH_2)_n-CH-CO-N-C-COOR$ with $R_2$, $R'$, $S-R_3''$ | | | | |
| Ex. No. | $R_3'$ | $R_2$ | n | | $R_1$ | R | $R_3'$ | $R_2$ | n | $R_1$ | R | $R_3''$ | $R_3'$ | n | $R_2$ | R' | R |
| 6. | $C_2H_5CO$ | H | 1 | | OH | $CH_3$ | { as in Column I } | | | { as in Column II } | | $C_2H_5$ | { as in Column I } | | | { as in Column II } | { as in Col. IV } |
| 7. | $CH_3CO$ | $C_2H_5$ | 1 | | Cl | $t-C_4H_9$ | | | | | | $CH_3$ | | | | | |
| 8. | $C_6H_5CO$ | H | 1 | | $CH_3O$ | $C_2H_5$ | | | | | | $C_6H_5$ | | | | | |
| 9. | $C_6H_5CO$ | $CH_3$ | 2 | | H | $CH_3$ | | | | | | $C_6H_5$ | | | | | |
| 10. | $CH_3CO$ | $CF_3$ | 0 | | Br | $C_2H_5$ | | | | | | $CH_3$ | | | | | |
| 11. | $C_3H_7CO$ | H | 2 | | OH | $t-C_4H_9$ | | | | | | $C_3H_7$ | | | | | |
| 12. | $CH_3CO$ | $CH_3$ | 1 | | H | $CH_3$ | | | | | | $C_2H_5$ | | | | | |
| 13. | $C_2H_5CO$ | H | 0 | | $C_2H_5O$ | $t-C_4H_9$ | | | | | | $CH_3$ | | | | | |

EXAMPLES 14 TO 21

By following the procedure of Example 1, Part C, employing as a starting material, the compounds of Examples 6 to 13 listed in Column V of Table I, the corresponding free acids of the compounds listed in Column V are obtained.

EXAMPLES 22 TO 29

By following the procedure of Example 1, Part D, employing as a starting material, the free acid compounds of Examples 14 to 21, the corresponding 3-mercapto-1-(3-mercapto-1-oxoalkyl)proline derivatives are obtained.

EXAMPLE 30

[1(S),cis]-1-(3-Mercapto-2-methyl-1-oxopropyl)-3-phenoxy-DL-proline

A. 3-Bromo-1-pyrroline-2-carboxylic acid, t-butyl ester

A mixture of Δ-1-pyrroline-2-carboxylic acid t-butyl ester (9.25 g, 50 mmole) (prepared as described in Example 2A) in toluene (70 ml) with n-bromosuccinimide (8.9 g, 50 mmole) is heated at reflux while exposed to a GE sunlamp (2 inches away) for 1 hour. During this time the succinimide is produced and the reaction is cooled to room temperature. The succinimide is removed by filtration and the filtrate evaporated to dryness. The residue is distilled in a Kugelrohr at 80° pot temperature yielding 3.5 g of product which is ½ starting material by C-13 NMR. This is used in the next step without purification.

B. 3-Phenoxy-1-pyrroline-2-carboxylic acid, t-butyl ester

A mixture of the material produced in part A and thallium phenoxide (3.9 g, 13 mmole) in dry dimethylformamide (30 ml) is stirred at room temperature under argon for 24 hours. The solvent is removed under vacuum and the residue diluted with ether to precipitate thallium bromide. This is removed by filtration and the filtrate concentrated, yielding an oil that is purified by distillation in a Kugelrohr apparatus. After 2 hours at 0.005 mm and 80° C. the material left in the distillation flask is nearly pure phenoxy compound (1.48 g) and is used in the next step with no further purification.

C. 3-Phenoxyproline

A mixture of the above ester, 1 N NaOH (5 ml) and 80% dioxane/water (20 ml) is stirred at room temperature for 4 hours. The solvents are removed under vacuum and the residue dissolved in water (25 ml) and treated with NaBH$_4$ (168 mg) over a 1 hour period at room temperature. The mixture is acidified (2 N HCl) to pH 6 and the solution kept at 0° for 16 hours whereupon crystals of the trans amino acid precipitate (∼25 mg). These are removed by filtration and the filtrate desalted by passage through a Dowex 50WX8 column (1"×12") using 1 N NH$_4$OH as the eluent. The uv active fractions are combined and concentrated to give a solid (616 mg) which is used in the Shotten-Baumann reaction without further purification.

D. [1(S),cis]-1-(3-Acetylthio-2-methyl-1-oxopropyl)-3-phenoxy-DL-proline

The above amino acid is slurried in water (20 ml) at 5° C. and the pH adjusted to 8.0 with solid Na$_2$CO$_3$. A solution of 3-acetylthio-2-methylpropanoyl chloride (550 mg, 2.5 mmole) in ether (1 ml) is added to the above and the pH of the reaction mixture kept between 7.3 and 8.2 for the next 1.5 hours by addition of Na$_2$CO$_3$. The mixture is washed with EtOAc (2×20 ml), acidified to pH 2 (10% HCl) and extracted with EtOAc (3×50 ml). The extracts are combined, dried (MgSO$_4$) and concentrated to yield an oil (810 mg). This is purified by flash column chromatography on silica gel (LP-1, 300 ml) using 10–20% HOAc-toluene mixture as eluents. Yield=530 mg.

E. [1(S),cis]-1-(3-Mercapto-2-methyl-1-oxopropyl)-3-phenoxy-DL-proline

The above acetyl-thio compound is dissolved in 50/50 concentrated NH$_4$OH/H$_2$O (degassed by bubbling argon through the solution for 15 minutes) under argon and stirred at room temperature for 1.5 hours. The slightly cloudy solution is adjusted to pH 6.5 with concentrated HCl (some warming occurs) and extracted with CH$_2$Cl$_2$ (2×25 ml). The pH is then adjusted to 1 and the solution again extracted with CH$_2$Cl$_2$ (3×50 ml). The extracts are combined, dried (MgSO$_4$) and concentrated yielding 410 mg of a glassy compound. Trituration with CHCl$_3$ results in crystallization. The solid is recrystallized from EtOAc-hexane yielding 261 mg of material, m.p. 134°–155° (mixture of diastereometers).

EXAMPLES 31 TO 38

Following the procedure of Example 30 except by substituting the 1-pyrroline-2-carboxylic acid ester shown in Column I of Table II set out below for the 1,2-dehydroproline, t-butyl ester, and the thallium compound shown in Column II for the thallium phenoxide, the compound shown in Column III is obtained; by substituting the acid chloride shown in Column IV for the 3-acetylthio-2-methyl propanoyl chloride, the compound shown in Column V is obtained.

TABLE II

| | Column I | | Column II | Column III | | Column IV | | | Column V | | | | |
|---|---|---|---|---|---|---|---|---|---|---|---|---|---|
| | $R_1$ $N=C-COOR$ | | TlOR$_6$ | $R_1$ $O-R_6$ $HN-C-COOH$ | | $R'_3-S-(CH_2)_n-\overset{R_2}{\underset{|}{CH}}-COCl$ | | | $R'_3S-(CH_2)_n-\overset{R_2}{\underset{|}{CH}}-CO-N-\overset{R_1}{\underset{|}{C}}-COOR$ | | | | |
| Ex. No. | $R_1$ | R | $R_6$ | $R_1$ | $R_6$ | $R'_3$ | $R_2$ | n | $R'_3$ | $R_2$ | n | R | $R_1$ | $R_6$ |
| 31. | OH | CH$_3$ | CH$_3$ | ⏜ as in Col. I | ⏜ as in Col. II | C$_2$H$_5$CO | H | 1 | ⏜ as in Col. IV | ⏜ as in Col. I | | | ⏜ as in Col. III | |
| 32. | Cl | t-C$_4$H$_9$ | C$_6$H$_5$ | | | CH$_3$CO | C$_2$H$_5$ | 1 | | | | | | |
| 33. | CH$_3$ | C$_2$H$_5$ | C$_2$H$_5$ | | | C$_6$H$_5$CO | H | 1 | | | | | | |
| 34. | H | CH$_3$ | C$_6$H$_5$ | | | C$_6$H$_5$CO | CH$_3$ | 2 | | | | | | |

TABLE II-continued

| | Column I | | Column II | Column III | | Column IV | | | Column V | | | | | |
|---|---|---|---|---|---|---|---|---|---|---|---|---|---|---|
| | $\underset{N=C-COOR}{\overset{R_1}{|}}$ | | $TlOR_6$ | $\underset{HN-C-COOH}{\overset{R_1}{|}}\overset{O-R_6}{|}$ | | $R'_3-S-(CH_2)_n-\overset{R_2}{\underset{|}{CH}}-COCl$ | | | $R'_3S-(CH_2)_n-\overset{R_2}{\underset{|}{CH}}-CO-N-\overset{R_1}{\underset{|}{C}}-COOR$ with $OR_6$ | | | | | |
| Ex. No. | $R_1$ | R | $R_6$ | $R_1$ | $R_6$ | $R'_3$ | $R_2$ | n | $R'_3$ | $R_2$ | n | R | $R_1$ | $R_6$ |
| 35. | Br | $C_2H_5$ | $CH_3$ | | | $CH_3CO$ | $CF_3$ | 0 | | | | | | |
| 36. | OH | t-$C_4H_9$ | $C_6H_5$ | | | $C_3H_7CO$ | H | 2 | | | | | | |
| 37. | H | $CH_3$ | $C_2H_5$ | | | $CH_3CO$ | $CH_3$ | 1 | | | | | | |
| 38. | $C_2H_5O$ | t-$C_4H_9$ | $C_3H_7$ | | | $C_2H_5CO$ | H | 0 | | | | | | |

EXAMPLES 39 TO 46

By following the procedure of Example 30, part E, employing as a starting material the compounds of Examples 31 to 38 of Table II, corresponding (3-mercapto-1-oxoalkyl)-3-alkoxy or 3-phenoxy-proline derivatives are obtained.

EXAMPLES 47 TO 54

By following the procedure of Example 1D, employing as a starting material the compounds of Examples 39 to 46, the corresponding (3-mercapto-1-oxoalkyl)-3-hydroxyproline derivatives are obtained.

What is claimed is:
1. A compound of the formula

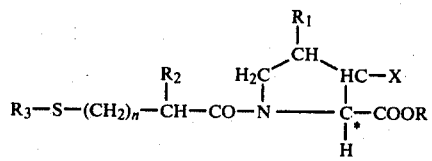

and physiologically acceptable basic salts thereof;
X is SH, lower alkoxy, lower alkylthio, hydroxy, phenylthio, phenyloxy, biphenylthio, biphenyloxy, 1-naphthylthio, 1-naphthyloxy, 2-naphthylthio, 2-naphthyloxy, substituted phenylthio or substituted phenyloxy wherein the substituents on the above phenyl groups are one or two halogens, hydroxy, lower alkyl, lower alkoxy, lower alkylthio, cyano or nitro groups;
R is hydrogen or lower alkyl;
$R_1$ is hydrogen, hydroxy, halogen or lower alkoxy, with the proviso that when $R_1$ is hydrogen, X can only be SH, and $R_1$ and X cannot both be hydroxy;
$R_2$ is hydrogen, lower alkyl or trifluoromethyl;
$R_3$ is hydrogen, $$R_4-\overset{O}{\underset{\|}{C}}-\text{ or}$$

$$-S-(CH_2)_n-\overset{R_2}{\underset{|}{CH}}-CO-N\underset{\underset{N}{|}}{\overset{\overset{R_1}{\underset{|}{CH}}}{\underset{H_2C}{\diagup}}\diagdown\overset{HC-X}{\underset{*}{\overset{|}{C}-COOR}}}$$

$R_4$ is lower alkyl or phenyl; and
n is 0, 1 or 2.
2. The compound of claim 1 wherein X is SH.
3. The compound of claim 1 wherein $R_1$ is hydrogen, $R_2$ is hydrogen and n is 1.
4. The compound of claim 1 wherein $R_3$ is hydrogen.
5. The compound of claim 1 wherein the proline ring is in the L-configuration.
6. The compound of claim 1 wherein X is in the trans configuration.
7. The compound of claim 1 wherein X is SH, $R_1$ is hydrogen, $R_2$ is hydrogen and $R_3$ is hydrogen.
8. The compound of claim 1 having the name (trans) 3-mercapto-1-(3-mercapto-1-oxopropyl)proline.
9. A composition useful in the treatment of hypertension comprising an effective amount of a compound of claim 1 and a pharmaceutically acceptable carrier therefor.
10. A method for reducing blood pressure in hypertensive mammals which comprises administering an effective amount of the composition of claim 9.

* * * * *

UNITED STATES PATENT AND TRADEMARK OFFICE
CERTIFICATE OF CORRECTION

PATENT NO. : 4,307,110

DATED : December 22, 1981

INVENTOR(S) : Michael E. Condon et al.

It is certified that error appears in the above-identified patent and that said Letters Patent are hereby corrected as shown below:

On The Title Page, in the Abstract, the general formula should read

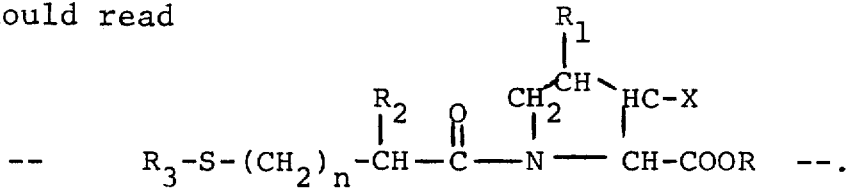

In the following formulae, " $R_3'$ " should read -- $R'_3$ -- :

Column 2, formula II
Column 3, first formula
Column 3, formula V
Column 5, formula X
Column 5, formula XI
Column 6, formula X
Column 6, formula XVI
Column 13, Table I, Column I, 2 occurrences
Column 13, Table I, Column III, 2 occurrences
Column 13, Table I, Column V.

In the following formulae, " $R_3''$ " should read -- $R''_3$ -- :

Column 3, first formula
Column 3, formula V
Column 4, formula VIb, 2 occurrences
Column 13, Table I, Column IV, 2 occurrences
Column 13, Table I, Column V, 2 occurrences.

Column 3, line 57, "product" should read --products--.
Column 9, line 21, "(Mercapto" should read --Mercapto--.
Column 11, line 58, "water" should read --ether--.

UNITED STATES PATENT AND TRADEMARK OFFICE
CERTIFICATE OF CORRECTION

PATENT NO. : 4,307,110

DATED : December 22, 1981

INVENTOR(S) : Michael E. Condon et al.

It is certified that error appears in the above-identified patent and that said Letters Patent are hereby corrected as shown below:

Columns 17 and 18, Table II, Column III, under the heading "$R_1$" insert -- ⏟ --; as in Col. I under the heading "$R_6$" insert -- ⏟ --' as in Col. II under the headings "$R'_3$  $R_2$  n" insert -- ⏟ --; as in Col. IV under the headings "R  $R_1$" insert -- ⏟ --; as in Col. I under the heading "$R_6$" insert -- ⏟ --. as in Col. III Signed and Sealed this Eighth Day of June 1982

|SEAL|

Attest:

Attesting Officer

GERALD J. MOSSINGHOFF

Commissioner of Patents and Trademarks